United States Patent [19]

Karrer

[11] 4,048,327

[45] Sept. 13, 1977

[54] (4-PHENOXYPHENOXY)ALKYL CYCLOPROPANECARBOXYLATES

[75] Inventor: Friedrich Karrer, Zofingen, Switzerland

[73] Assignee: Ciba-Geigy Corporation, Ardsley, N.Y.

[21] Appl. No.: 707,150

[22] Filed: July 20, 1976

[30] Foreign Application Priority Data

July 25, 1975 Switzerland ................. 9734/75
June 17, 1976 Switzerland ................. 7744/76

[51] Int. Cl.² .................. C07C 61/04; A01N 9/28
[52] U.S. Cl. .................................. 424/305; 560/124
[58] Field of Search ................ 260/468 H; 424/305

[56] References Cited

U.S. PATENT DOCUMENTS 3,957,849  5/1976  Henrick et al. ................. 260/468 H Primary Examiner—Lorraine A. Weinberger
Assistant Examiner—Michael Shippen
Attorney, Agent, or Firm—Harry Falber

[57] ABSTRACT

New cyclopropanecarboxylates of the formula

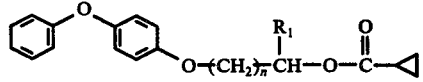

are disclosed, wherein $R_1$ represents hydrogen, methyl or ethyl and $n$ is 1, 2 or 3. These compounds are useful as pesticides, especially for the control of insects and pests of the order Acarina and cotton and vegetable plant pests.

13 Claims, No Drawings

(4-PHENOXYPHENOXY)ALKYL CYCLOPROPANECARBOXYLATES

The present invention provides new esters of cyclopropanecarboxylic acid, a process for their production and a method of using them in pest control.

The cyclopropanecarboxylates according to the invention have the formula I

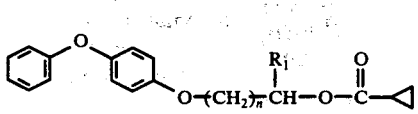

wherein $R_1$ represents hydrogen, methyl or ethyl and $n$ is 1, 2 or 3. Preferred compounds on account of their activity are those of the formula I, in which $R_1$ represents hydrogen or methyl and n is 1 or 2, but especially 1. The compounds of formula I can be prepared by methods which are known per se, for example in the following manner:

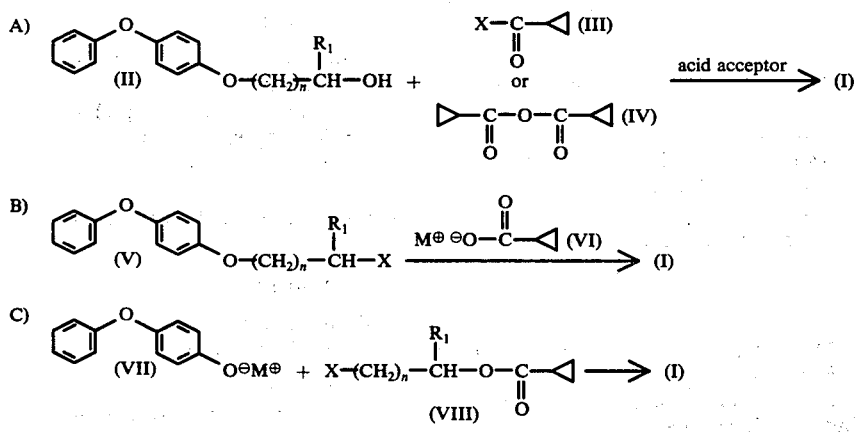

In the formulae II to VIII the symbols $R_1$ and $n$ have the meanings indicated for formula I, X represents a halogen atom, especially a chlorine or bromine atom, and M represents a metal of the 1$^{st}$ or 2$^{nd}$ groups of the Periodic Table, in particular sodium, potassium or calcium and also silver.

Examples of suitable acid acceptors are: tertiary amines, such as trialkylamines, pyridine, inorganic bases, such as hydrides, hydroxides, alkoxides and carbonates of alkali metals or alkaline earth metals.

The said processes A, B and C are carried out at temperatures of −10 to +100° C (process A with acid halide is preferably carried out between 0° and 30° C; with acid anhydride the range between 20° and 100° C is preferred; for process B a temperature range of 20° to 60° C is preferred and for process C one of 10° to 80° C is preferred), at atmospheric pressure and in inert solvents or diluents. Suitable examples of solvents or diluents for reaction A are: benzene, toluene, xylene, saturated aliphatic hydrocarbons, such as hexane, heptane; ethers, such as diethyl ether, tetrahydrofurane, dioxan, dimethoxyethane and esters, such as ethyl acetate; for reactions B and C dimethyl sulphoxide; dimethyl formamide; hexamethylphosphorotriamide; dimethoxyethane, and ketones, such as acetone, methyl ethyl ketone or cyclohexanone.

The starting materials of formulae II to VIII are known compounds or they can be prepared analogously to methods described in the literature.

The compounds of formula I are suitable for the control of various animal and plant pests, particularly for combating members of the order Acarina of the families: Ixodidae, Argasidae, Tetranychidae, Dermanyssidae, and insects of the families: Acrididae, Blattidae, Gryllidae, Gryllotalpidae, Terrigoniidae, Cimicidae, Pyrrhocoridae, Reduviidae, Aphididae, Delphacidae, Diaphididae, Pseudococoidae, Chrysomilidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Galliphoridae, Trypetidae, Pulicidae. Compounds of formula I are suitable for the control of storage pests. They are particularly useful for the control of harmful insects in cotton plantations and vegetable crops.

The insecticidal action of the compounds of formula I can be substantially broadened and adjusted to prevailing conditions by adding other insecticides or acaricides.

Examples of suitable additives are: organic phosphorus compounds, nitrophenols and their derivatives; formamidines, ureas, carbamates, chrysanthemates and derivatives or chlorinated hydrocarbons.

The compound of formula I can be used as pure active substance or together with suitable carriers and/or additives. Suitable carriers or additives may be solid or liquid and correspond to the substances conventionally used in the art of formulation, for example: natural and regenerated substances, solvents, dispersing agents, wetting agents, stickers, thickeners, binders or fertilizers.

For application, the compounds of formula I can be processed to dusts, emulsion concentrates, granulates, dispersions, sprays, to solutions or suspensions in formulations well known to those skilled in the art of application.

The compositions of the present invention, which contain compounds of the formula I, are obtained in known manner by intimately mixing and/or milling active substances of formula I with suitable carriers, with or without the addition of dispersants or solvents which are inert to the active ingredients. The active compounds can be applied in the following application forms.

Solid preparations: dusts, tracking agents, granulates (coated granulates, impregnated granulates and homogranulates);

Liquid preparations:
a. water-dispersible active substance concentrates: wettable powders, pastes or emulsion;
b. solutions.

The content of active substance in the compositions described above is between 0.1 and 0.1 and 95 percent by weight.

The active substances of formula I can be formulated for example in the following way:

Dusts:

The following substances are used for the preparation of a) a 5% b) a 2% dust:
a. 5 parts of active substance, 95 parts of talcum
b. 2 parts of active substance, 1 part of highly dispersed silicic acid, 97 parts of talcum.

The active ingredients are mixed and milled with the carriers.

Granulates:

The following substances are used to obtain a 5% granulate:
5 parts of active substance
0.25 parts of epichlorohydrin
0.25 parts of cetyl polyglycol ether
3.50 parts of polyethylene glycol
91 parts of kaolin (particle size 0.3–0.8 mm).

The active substance is mixed with epichlorohydrin and dissolved in 6 parts of acetone, then the polyethylene glycol and cetyl polyglycol ether are added. The resultant solution is sprayed onto kaolin and the acetone is subsequently evaporated in vacuo.

Wettable Powder

The following ingredients are used to prepare: (a) a 40%, (b) and (c) a 25% and (d) a 10% wettable powder.
a. 40 parts of active substance, 5 parts of sodium lignin sulphonate, 1 part of sodium dibutyl-naphthalenesulphonate, 54 parts of silicic acid;
b. 25 parts of active substance, 4.5 parts of calcium lignin sulphonate, 1.9 parts of Champagne chalk/hydroxyethyl cellulose mixture (1:1), 1.5 parts of sodium dibutyl naphthalenesulphonate, 19.5 parts of silicic acid, 19.5 parts of Champagne chalk, 28.1 parts of kaolin;
c. 25 parts of active substance, 2.5 parts of isooctylphenoxy-polyoxyethyleneethanol, 1.7 parts of Champagne chalk/hydroxyethyl cellulose mixture (1:1), 8.3 parts of sodium aluminium silicate, 16.5 parts of infusorial earth, 46 parts of kaolin;
d. 10 parts of active substance, 3 parts of a mixture of the sodium salts of saturated fatty alcohol sulphates, 5 parts of naphthalenesulphonic acid/formaldehyde condensate, 82 parts of kaolin.

The active substances are intimately mixed in suitable mixers with the additives, and the mixture is then milled in appropriate rolling-mills. Wettable powders are obtained which can be diluted with water to give suspensions of any desired concentration.

Emulsifiable concentrates:

The following substances are used to produce (a) a 10%, (b) a 25%, and (c) a 50% emulsifiable concentrate:
a. 10 parts of active substance, 3.4 parts of epoxidised vegetable oil, 3.4 parts of a combination emulsifier consisting of fatty alcohol polyglycol ether and alkylarylsulphonate calcium salt, 40 parts of dimethyl formamide, 43.2 parts of xylene;
b. 25 parts of active substance, 2.5 parts of epoxidised vegetable oil, 10 parts of alkylarylsulphonate/fatty alcohol polyglycol ether mixture, 5 parts of dimethyl formamide, 57.5 parts of xylene;
c. 50 parts of active substance, 4.2 parts of tributylphenol-polyglycol ether, 5.8 parts of calcium-dodecylbenzenesulphonate, 20 parts of cyclohexanone, 20 parts of xylene.

By diluting these concentrates with water it is possible to obtain emulsions of any required concentration.

Spray:

The following ingredients are used to prepare (a) a 5% spray, and (b) a 95% spray:
a. 5 parts of active substance, 1 part of epichlorohydrin, 94 parts of ligroin (boiling range 160°–190° C);
b. 95 parts of active substance, 5 parts of epichlorohydrin.

The invention is further illustrated by the following Examples.

EXAMPLE I

Production of 3-(4-phenoxy)-phenoxy-1-cyclopropylcarbonyloxy-propane

To a solution of 19.5 g of 3-(4-phenoxy)-phenoxy-propanol (m.p. 62°–63° C) in 100 ml anhydrous toluene are added 10.1 g of triethylamine and subsequently 10.5 g cyclopropanecarboxylic acid chloride are added dropwise in the course of approximately half an hour at 10°–15° C with stirring. The stirring of the reaction mixture is continued for 14 hours at room temperature, and thereafter the reaction mixture is successively and repeatedly washed with water, dilute HCl, 10% sodium carbonate solution and is finally washed neutral with sodium chloride solution. The organic phase is separated, dried over sodium sulphate, and the solvent is evaporated in vacuo. The residue, which solidifies to a crystalline state, is recrystallized from cyclohexane to yield pure 3-(4-phenoxy)-phenoxy-1-cyclopropylcarbonyloxy-propane (m.p. 48°–49° C). The following compounds of formula I are obtained in analogous manner:

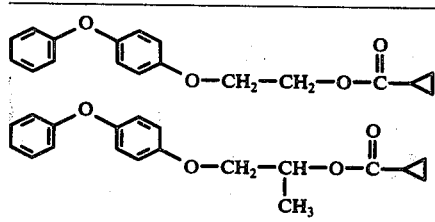

m.p. 40–42° C $n_D^{20}$: 1.5479

-continued

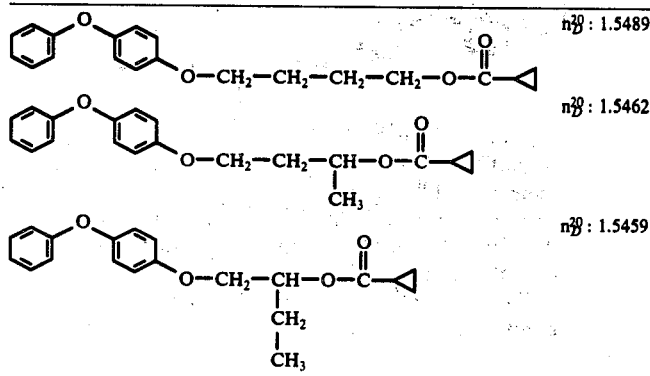

$n_D^{20}$: 1.5489

$n_D^{20}$: 1.5462

$n_D^{20}$: 1.5459

EXAMPLE 2

A. Contact action on *Dysdercus fasciatus* larvae

A specific amount of a 0.1% solution of active compound in acetone (corresponding to 10 mg active substance/m²) was pipetted into an aluminium dish and dispersed homogeneously.

After evaporation of the acetone, 10 larvae of *Dysdercus fasciatus* in the fifth stage were put into the dishes containing feed and moist cotton wool. The dish was then covered with a screen top.

After about 10 days, i.e. after the untreated controls had shed and emerged fully to the adult stage, the treated test subjects were examined for the number of normal adults. The compounds of formula I displayed good activity in the above test.

B. Contact action on *Tenebrio molitor* pupae

A specific amount of a 0.1% solution of active substance in acetone, corresponding to 10 mg active substance/m², was pipetted into an aluminium dish and homogeneously dispersed.

After evaporation of the acetone, 10 pupae which had just shed their cocoon were placed onto the treated plate. The dish was covered with a screen top.

After the untreated controls had emerged from the pupae cocoon as imagines, the test subjects were examined for the number of adults.

The compounds of formula I showed good activity in the above test.

EXAMPLE 3

Action on spider mites

*Phaseolus vulgaris* (dwarf beans) were infected with an infested piece of leaf from a mass culture of *Tetranychus urticae* 12 hours before testing for acaricidal activity. The mobile stages which have migrated to the plants were sprayed with the emulsified test preparations from a chromatography atomiser in a concentration of 0.04% so that the spray broth did not run off.

After two to seven days the number of dead and living larvae, adults and eggs were evaluated under a stereoscopic microscope and the result was expressed in percentages. During the intervening period the treated plants were kept in greenhouse compartments at 25° C.

The compounds of formula I were found to act in this test on eggs, larvae and adults of *Tetranychus urticae*.

EXAMPLE 4

Action on ticks:

A. *Rhipicephalus bursa*

5 adult ticks and 50 tick larvae were counted into each of a number of test tubes and immersed for 1 to 2 minutes in 2 ml of an aqueous emulsion at a concentration of 100, 10, 1 or 0.1 ppm of test substance of formula I respectively. The tube was then sealed with a cotton wool plug and turned upside down to enable the cotton wool to absorb the emulsion of the active substance.

The adults were evaluated after 2 weeks and the larvae after 2 days.

B. *Boophilus microplus* (larvae)

20 sensitive and 20 OP-resistant larvae were tested in a dilution series analogous to the one used in test A. (the resistance refers to the tolerance towards diazinone).

The substances of formula I acted in these tests on adults and larvae of *Rhipicephalus bursa* and OP-sensitive and OP-resistant larvae of *Boophilus microplus*.

EXAMPLE 5

Action on eggs of *Spodoptera littoralis*

Eggs of *Spodoptera littoralis* were immersed in a 0.05% solution of active compound in acetone. The treated eggs were then kept in plastic dishes at 21° C and 60% relative humidity. After 3 to 4 days the hatching out rate was determined. Compounds of formula I acted well on eggs of Spodoptera littoralis in this test.

EXAMPLE 6

Action on eggs of *Tribolium castaneum*

5 Parts by weight of active substance of formula I and 5 parts by weight of talcum are mixed and finely ground. By further admixture of 90 parts by weight of talcum a 5% dusting powder is obtained, which is used as starting mixture for a dilution series of active substance for the activity test against the storage pest *Tribolium castaneum*.

50 g of wheat flour were mixed with appropriate quantities of the dusting powder described above to obtain concentrations of active compound of 0.1, 0.05 and 0.01% by weight and these mixtures were charged into beakers. 25 beetles were put into each beaker containing 25 g flour. After 3 days the beetles were sieved out again. The eggs laid in the flour during this time formed the infestation. The evaluation took place on the basis of the population changes within a period of 8 weeks.

Compounds of formula I were found to show good activity in the above test.

What is claimed is:

1. A cyclopropanecarboxylate of the formula I

(I)

wherein
R$_1$ represents hydrogen, methyl or ethyl and
n is 1, 2 or 3.

2. A cyclopropanecarboxylate according to claim 1, wherein
R$_1$ represents hydrogen or methyl and
n is 1 or 2.

3. A cyclopropanecarboxylate according to claim 1, wherein
R$_1$ represents hydrogen.

4. A cyclopropanecarboxylate according to claim 1, wherein
n is 1.

5. The cyclopropanecarboxylate according to claim 3 of the formula

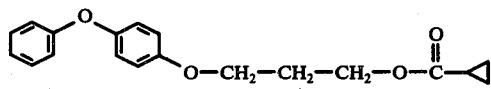

6. The cyclopropanecarboxylate according to claim 2 of the formula

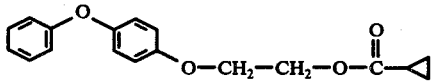

7. The cyclopropanecarboxylate according to claim 2 of the formula

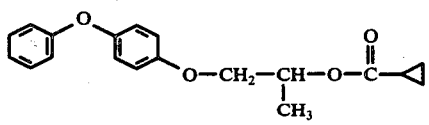

8. An insecticidal and acaricidal composition comprising as active ingredient an insecticidally and acaricidally effective amount of a cyclopropanecarboxylate of the formula I according to claim 1 in admixture with a suitable carrier therefor.

9. The composition of claim 8, wherein said active ingredient corresponds to the formula

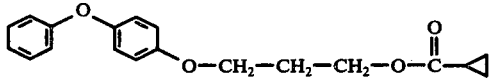

10. The composition of claim 8, wherein said active ingredient corresponds to the formula

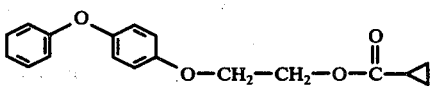

11. The composition of claim 8, wherein said active ingredient corresponds to the formula

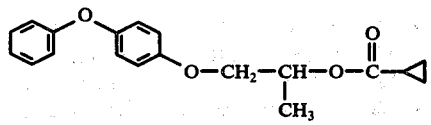

12. A method for combatting insects and acarids, which comprises applying thereto or to the locus thereof an insecticidally and acaricidally effective amount of at least one cyclopropanecarboxylate of the general formula I as defined in claim 1.

13. The method according to claim 12, wherein said locus is cotton and vegetables plants.

* * * * *